United States Patent [19]

Rock

[11] 4,203,891

[45] May 20, 1980

[54] METHOD OF COLLECTING ANTI-HEMOPHILIC FACTOR VIII FROM BLOOD AND BLOOD PLASMA USING HEPARIN OR SODIUM HEPARIN

[76] Inventor: Gail A. Rock, 270 Sandridge Rd., Ottawa, Ontario, Canada

[21] Appl. No.: 865,656

[22] Filed: Dec. 29, 1977

[30] Foreign Application Priority Data

Dec. 19, 1977 [CA] Canada ................................. 293393

[51] Int. Cl.$^2$ ............................................. C07G 7/00
[52] U.S. Cl. ............................. 260/112 B; 424/101; 424/177; 424/183
[58] Field of Search ................... 260/112 B; 424/101, 424/183

[56] References Cited

U.S. PATENT DOCUMENTS

| | | | |
|---|---|---|---|
| 2,847,348 | 8/1958 | Singher et al. | 424/177 X |
| 2,867,567 | 1/1959 | Bidwell | 260/112 B |
| 3,453,194 | 7/1969 | Bennett et al. | 424/183 |
| 3,548,052 | 12/1970 | Kolt | 424/183 |
| 3,631,018 | 12/1971 | Shanbrom et al. | 260/112 B |
| 3,652,530 | 3/1972 | Johnson et al. | 260/112 B |
| 3,682,881 | 8/1972 | Fekete et al. | 260/112 B |
| 3,803,115 | 4/1974 | Fekete et al. | 260/112 B |
| 3,891,622 | 6/1975 | Mardiguian et al. | 424/183 |
| 4,069,216 | 1/1978 | Shanbrom | 260/112 B |
| 4,137,223 | 1/1979 | Shanbrom et al. | 260/112 B |

OTHER PUBLICATIONS

Proc. 7th Congress Europ. Soc. Haemat., London 1959, Part II, pp. 587–593 (1960), Blomback et al.
Transfusion, Jul.–Aug. 1975, vol. 15, No. 4, Pool, pp. 305–306.
Chem. Abstracts, vol. 56, 1962, 7847i–7848a, Mayer et al.
Chemistry for the Clinical Laboratory, 4th Ed., 1976, White et al., pp. 7–8.
Vox Sang–30: pp. 1–22 (1976), Vermeer et al.
Technical Manual, Am. Assoc. of Blood Banks, 7th Ed., 1977, pp. 54–57.
Thromb. Diath. Haemorrh. 14, pp. 32–51 (1965), Weiss.
Hematology, Williams et al., 1972, pp. 1329 and 1311–1312.
Principles of Biochemistry, 3rd Ed., 1959, White et al., p. 647.
Human Blood Coagulation and Its Disorders, 2nd Ed., Biggs et al., (1957), pp. 160–162.

*Primary Examiner*—Howard E. Schain
*Attorney, Agent, or Firm*—Pollock, Vande Sande and Priddy

[57] ABSTRACT

A method of greatly increasing the yield of anti-hemophilic Factor VIII (AHF) obtained from whole blood, blood plasma or plasma fractions based on the maintenance of physiological concentrations of calcium and/or other ions in the whole blood or plasma components.

7 Claims, No Drawings

METHOD OF COLLECTING ANTI-HEMOPHILIC FACTOR VIII FROM BLOOD AND BLOOD PLASMA USING HEPARIN OR SODIUM HEPARIN

This invention relates to a method for collecting anti-hemophilic factor (AHF, Factor VIII). More particularly, this invention relates to a method for improving the yield of AHF obtained from whole blood, blood plasma and/or plasma fractions.

Classic hemophilia A is a disease which is caused by the absolute or relative deficiency of anti-hemophilic factor (AHF) or Factor VIII in the blood. Until recently efforts to treat this disease were based on attempts to restore Factor VIII levels using frozen plasma or whole blood containing Factor VIII. However it was not possible to achieve optimal levels of the missing proteins (AHF) without causing considerable volume overload in the patient, due to the large volumes of plasma required.

In efforts to concentrate AHF, scientists have proposed various methods for the isolation of AHF or for the preparation of plasma fractions rich in AHF from human blood or animal blood.

In practice many of these methods have proven to be unreliable since the AHF activity of the fractions tends to be lost during the isolation.

Indeed the yield of AHF from the plasma by any method is low, therefore, in general, the cost of treatment is high. This difficulty in isolation is caused by the fact that Factor VIII is a labile protein present in plasma in only trace amounts, is difficult to separate completely from other plasma proteins, particularly fibrinogen, and is readily susceptible to denaturation by heat, freezing and continued storage.

The various methods of fractionating blood and blood plasma into separate components or concentrates are well known. Among the methods that are in use for the isolation of AHF are chromatography, batch adsorption and elution, and selective precipitation. Various precipitating agents that have been used are ethanol, ethyl ether, ammonium sulfate, phosphate-sodium citrate, amino acids, and cryoprecipitation procedures. Recently, the clinical use of a glycine-precipitated AHF fraction of whole plasma was disclosed.

An important landmark in hemophiliac treatment was the discovery that after thawing of frozen plasma at low temperatures a precipitate is obtained which is highly enriched in Factor VIII. This has provided a widely used method for small scale preparations of Factor VIII concentrates.

As well, various methods are known for extraction of the Factor VIII contained in the cryoprecipitate made from blood collected into ACD and CPD anticoagulants. These include using polyethylene glycol, glycine, ethanol and any of a number of combinations of the above procedures.

None of the above methods, however, has proved to be a completely practical method for isolating AHF since in all cases the relative recovery of AHF is low and the yields are highly variable.

Th reason for some of this variability is based on individual variation in Factor VIII levels in donor blood; other reasons are based on the various collection and processing techniques. In all some 90 variables have been identified which determine the Factor VIII yield in the cryoprecipitate (c.f. Pool, J. G. Cryoprecipitate Quality and Supply Transfusion, Vol. 15 No. 4, July-August 1975, p. 305).

Even under ideal conditions it does not appear to be possible to recover all of the AHF in the cryoprecipitate. The literature reports average recoveries of 35-45% in the cryoprecipitate and 10-20% in the cryoprecipitate supernatant with 50% variability in the mean values reported.

In summary, there is considerable loss of the total Factor VIII activity during the cryoprecipitation process. From 10-40% of the total AHF activity is not recoverable in cryoprecipitate or in the supernatant but is simply left unaccounted for. The only explanation given for this loss is the general lability of the protein and the fact that during collection and storage some of the Factor VIII is destroyed or denatured.

Recently it has been reported that the cold-precipitability of AHF is dependent on the molecular form of Factor VIII. That is, the heavier forms of the molecule will cryoprecipitate while the lighter forms do not. Specifically it has been found that upon ultra-centrifugation the cryoprecipitate activity was all in the fast or heavy molecular weight form while the activity in the supernatant was of a slow or relatively low molecular weight form.

There has been considerable discussion and controversy about the molecular structure of Factor VIII. Exact definition of this structure has not yet been made. However two general schools of thought exist. The first is that it is a high molecular weight glycoprotein with a total molecular weight of $10^6$ and is in fact composed of identical sub-units with molecular weights of 195,000 all of which are immunologically and biologically active. The second school of thought depends on the ability of this high molecular weight molecule to dissociate and be separated by agarose column chromatography in buffers which contain 0.25 M $CaCl_2$. The exact relationship of these salt dissociated components has not yet been defined. It has been found that the low molecular weight sub-unit continues to behave as a monomeric species when rechromatographed in the absence of 0.25 M $CaCl_2$. More recently, it has been reported that spontaneous reaggregation of the small fragment is observed if calcium is omitted from the buffer system although the addition of 0.002 M calcium (i.e. physiological concentration) is sufficient to prevent this.

One thing is clear however from previous work in this field; i.e. the essential role of calcium and/or other ions in determining the molecular forms of the Factor VIII molecule. As has been previously stated, the molecular form of the molecule would appear to determine the cryoprecipitability of the Factor VIII material and perhaps the stability of the low molecular weight component.

All previous AHF purification procedures have been based on the initial collection of whole blood into anticoagulants which function by chelating calcium ions, in particular ACD, CPD, EDTA, oxylates and a variety of other agents. This chelation of calcium results in the effective removal of this ion from the environment and since calcium is necessary for clot formation it prevents blood from clotting.

The present invention was designed to protect the normal physiological environment of the blood and plasma by maintaining physiological concentrations of calcium and/or other ions. It was to be expected that if the molecular form, the cryoprecipitability and indeed the stability of the Factor VIII molecule were dependent on calcium and/or other ions then the maintenance of normal levels of the(se) compound(s) would produce a better yield.

Thus, the present invention provides a method for recovering anti-hemophilic Factor VIII from whole blood or blood plasma which comprises collecting whole blood or blood plasma from a donor directly into an anticoagulant agent which does not alter the physiological concentrations of calcium or other ions in the whole blood or blood plasma and recovering the anti-hemophilic Factor VIII according to conventional recovery techniques.

The preferred anticoagulant agents found to be useful in the method of this invention include trypsin inhibitor, hirudin and heparin. The last agent, heparin is most preferred since it is more readily available and more economical to use. However, the other agents have been found to be equally effective. The anti-coagulation action of each of these agents is as follows:

Trypsin inhibitor—(soybean) which is antithromboplastic

Hirudin—prevents clotting by inhibiting thrombin action

Heparin—acts to prevent conversion of prothrombin to thrombin in the final step of the clotting procedure.

The preferred anticaogulant heparin is preferably employed in the range of from 0.1–10 units/ml, based on the total volume of blood collected. Hirudin may be used in the range of from 100 to 500 units/ml of whole blood while the trypsin inhibitor may be used in the range of from 2.5 to 25 mg/ml of whole blood.

In accordance with the invention, various known procedures for recovering AHF from whole blood or blood plasma may be employed. Any method or combination of methods for fractionating AHF is useful, in particular fractionating AHF 1. From fresh or frozen plasma by glycine, ethanol, ethanol-glycine, polyethylene glycol (PEG) or glycine-PEG precipitation and/or other known purification agents.

2. From cryoprecipitate by glycine, ethanol, ethanol-glycine, PEG or glycine-PEG precipitation and/or other known purification agents.

Fractionations of this type are well known in the art. Reference can be made to American National Red Cross U.S. Pat. No. 3,652,530 issued Mar. 28, 1972 for a description of PEG fractionation methods and Baxter Laboratories, Inc. U.S. Pat. No. 3,631,018 issued Dec. 28, 1971 for PEG-glycine fractionation techniques.

The PEG is a high molecular weight polymer which is generally produced by reacting ethylene oxide with ethylene glycol or water and has the following structure $HO(C_2H_4O)_nC_2H_4OH$ in which n represents the average number of oxyethylene groups. The PEG should be non-toxic and preferably ranges in molecular weight from about 200 to about 20,000. More preferably, it has a molecular weight in the range of from about 440 to about 6,000.

In the present method virtually all of the AHF present in the blood is recoverable in the plasma and in the PEG fraction from the plasma. As well very high levels of AHF are found in the cryoprecipitate and following further purification of the cryoprecipitate by any of the known methods, such as centrifugation or filtration to remove any insoluble matter or column or batch chromatography techniques.

The method is preferably applied to the rcovery of Factor VIII from whole human blood or human blood plasma.

The following examples illustrate the present invention. All parts and percentages are by weight unless otherwise indicated.

EXAMPLE 1

A high yield of Factor VIII in plasma and in cryoprecipitate is produced in the following manner. Blood was collected from random male and female donors into standard Fenwal blood bags containing sodium heparin. A quantity of 7–8 units/ml of plasma was used, based on the total volume of blood collected (this is approximately 3–5 units of heparin/ml of whole blood).

Red cells were separated from plasma by centrifugation and the plasma was collected for testing or for cryoprecipitate production according to standard procedures.

In order to demonstrate that this procedure would increase the Factor VIII recovery, when compared to the usual modes of collection, blood from a single donor was separately collected into one bag containing heparin as anticoagulant and as well blood from the same donor was collected into another bag containing CPD as anticoagulant. This was repeated for six individual donors and a comparison was made of the Factor VIII recovered in the two cases. The results from these 6 donors are shown in the following Table 1.

In the table it is seen that the total Factor VIII activity in the whole blood is much higher when calcium was retained: 215 units versus 177 units for CPD collected blood. As well this higher activity leads to a greater recovery in the cryoprecipitate: 166 units versus 76.3 when the calcium was chelated.

TABLE 1

| | AHF YIELD | | | | | |
| --- | --- | --- | --- | --- | --- | --- |
| | Plasma | | Cryoprecipitate | | Cryosupernatant | |
| Anticoagulant | Total units | % Recovery initial | Total units | % Recovery initial | Total units | % Recovery initial |
| CPD (Calcium removed) | 177 | 100 | 76.3 | 43.1 | 34.0 | 19.2 |
| Heparin (Calcium present) | 215 | 100 | 166.0 | 77.2 | 41.7 | 19.4 |

EXAMPLE 2

The procedure of Example 1 was repeated on 10 random donors to demonstrate reproducibility of the data. Each donor gave a full unit (450 cc) of blood into a bag containing heparin as sole anticoagulant.

TABLE 2

| AHF levels in 10 donors: whole blood collected directly into at time of donation. | | | |
| --- | --- | --- | --- |
| | Plasma | Cryoprecipitate | Cryosupernatant |
| Units: | 293 ± 30.4 | 227 ± 28.4 | 61.2 ± 19.0 |
| % recovery: | 100% | 78% ± 8.8 | 21% ± 5 |

Yields of Factor VIII in both the plasma and the cryoprecipitate are significantly increased over usual recoveries.

EXAMPLE 3

The procedures of Example 1 were repeated with further purification of the plasma or cryoprecipitate derived from said plasma using one of the agents commonly employed for this purpose: polyethylene glycol (PEG) molecular weight 4000.

The AHF concentrates were prepared in the following manner at room temperature. Plasma was adjusted to pH 6.3 with 0.1 N acetic acid and sufficient PEG was added to bring the final concentration to about 4.5%. The mixture was then gently agitated for 10 minutes at room temperature and then centrifuged at 3250×g for 15 minutes. The supernatant was decanted and the precipitate was discarded. The supernatant was then adjusted to pH 6.0 with 0.1 N acetic acid or NaOH as required and the PEG concentration was brought to about 11%. The mixture was gently agitated for 45 minutes and then centrifuged at 2000×g for 10 minutes to sediment the precipitate. Th supernatant was decanted and the precipitate from CPD samples was redissolved in glycine-citrated saline buffer, pH 7.2. The precipitates from the heparin samples were put in the same buffer containing 1 unit heparin U.S.P. per ml (pH 7.2).

The results of these fractionations are shown in Table 3.

TABLE 3

|  | Anticoagulant | |
|---|---|---|
|  | CPD | Heparin |
| Plasma |  |  |
| Total AHF units | 177 | 215 |
| 4.5-11% PEG-precipitate |  |  |
| AHF units | 111.5 | 206.4 |
| Recovery (%) | 63.0 | 96.0 |
| Cryoprecipitate |  |  |
| Total AHF units | 76.1 | 166 |
| 4.5-11% PEG-precipitate |  |  |
| AHF units | 46.4 | 116.2 |
| Recovery (%) | 61.0 | 70.0 |

It can be seen from these results that the percent recovery after PEG fractionation in all fractions is much higher when the calcium environment is maintained.

From the starting plasma, PEG precipitation of plasma resulted in 206.4 units with calcium present and 111.5 with it removed. Comparable values for PEG recovery from cryoprecipitate are 116.2 and 46.4 units. These values are statistically significant at all levels.

The relative percentage improvement in yields when physiological levels of calcium and/or other ions were maintained is shown in Table 4. Marked improvement in Factor VIII recovery was noted in all cases.

TABLE 4

% Improvement on Yield of AHF when Physiological Concentration of Ions is Maintained. Expressed as % Improvement Compared to Recoveries in CPD.

| | |
|---|---|
| Whole plasma | 21% |
| 4.5-11% PEG precipitate of plasma | 85% |
| Cryoprecipitate | 118% |
| 4.5-11% PEG precipitate of cryoprecipitate | 150% |

EXAMPLE 4

The stability of the AHF made according to this invention is much improved over normal. The procedures of Example 3 were followed except that the PEG precipitates from plasma and cryoprecipitate were resuspended in water and allowed to stand at room temperature (25° C.) for 24 hours. Assays were done at 8, 18 and 24 hours. The samples in which the physiological concentration of calcium and/or other ions were maintained retained 98% of the initial AHF activity after 24 hours. When calcium was removed by collection into CPD the AHF showed only 75% activity at this time.

In Table 5 there is reproduced the data found in Table 1 along with similar data for the combined anticoagulants CPD and heparin. Although the combined anticoagulants show better recovery values for Factor VIII than the CPD anticoagulant alone, the combined anticoagulants are not as effective as the heparin anticoagulant alone.

TABLE 5

| | AHF YIELD | | | | | |
|---|---|---|---|---|---|---|
| | Plasma | | Cryoprecipitate | | Cryosupernatant | |
| Anticoagulant | Total Units | % Recovery | Total Units | % Recovery | Total Units | % Recovery |
| CPD (Calcium removed) | 177 | 100 | 76.3 | 43.1 | 34.0 | 19.2 |
| CPD + Heparin added (Calcium removed) | 187 | 100 | 102.8 | 55 | 44.9 | 24 |
| Heparin (Calcium present) | 215 | 100 | 166 | 77.2 | 41.7 | 19.4 |

In Table 6 there is shown the data of Table 3 in conjunction with similar data for the combined anticoagulants CPD and heparin. Again the heparin anticoagulant alone produces better results than either CPD alone or CPD and heparin combined. The actual improvement, expressed as percent is shown in the table also.

TABLE 6

| | Anticoagulant | | |
|---|---|---|---|
| | CPD | CPD + Heparin | Heparin |
| Plasma |  |  |  |
| Total units AHF | 177 | 187 | 215 |
| 4.5 – 11% PEG-precipitate |  |  |  |
| AHF units | 111.5 | 136.6 | 206.4 |
| % Recovery | 63.0 | 74.1 | 96.0 |
| Cryoprecipitate |  |  |  |
| Total units AHF | 76.1 | 103.8 | 166.0 |
| 4.5 – 11% PEG-precipitate |  |  |  |
| AHF Units | 46.4 | 61.8 | 116.2 |
| % Recovery | 61 | 60 | 70 |

| | % Improvement | |
|---|---|---|
| | Heparin/CPD + Heparin | Heparin/CPD |
| Plasma | 15% | 21% |
| Plasma PEG-precipitate | 51% | 85% |
| Cryo | 60% | 118% |
| Cryo PEG-precipitate | 88% | 150% |

I claim:

1. A method for recovering antihemophilic Factor VIII from whole blood or blood plasma or blood plasma fractions which comprises collecting whole blood or blood plasma or blood plasma fractions from a donor directly into an anticoagulant agent selected from the group of heparin, sodium heparin, or mixtures thereof which agent does not reduce the physiological concentration of calcium in the whole blood or blood plasma or flood plasma fraction and recovering the desired antihemophilic Factor VIII.

2. A method as claimed in claim 1 wherein the anticoagulant agent is heparin.

3. A method as claimed in claim 2 wherein the anticoagulant agent is sodium heparin.

4. A method as claimed in claim 3 wherein from 0.1–10 units/ml anticoagulant based on the total volume of whole blood or blood plasma collected is employed.

5. A method as claimed in claim 1 wherein the Factor VIII is recovered by fractionating Factor VIII from fresh or frozen blood plasma by one or more precipitations selected from glycine, ethanol, ethanol-glycine, polyethylene glycol and glycine-polyethylene glycol precipitations.

6. A method as claimed in claim 1 wherein the Factor VIII is recovered by fractionating Factor VIII from a blood plasma cryoprecipitate by one or more precipitations from glycine, ethanol, ethanol-glycine, polyethylene glycol or glycine-polyethylene glycol precipitations.

7. A method as claimed in claim 1 wherein whole human blood or human blood plasma is collected.

* * * * *

UNITED STATES PATENT AND TRADEMARK OFFICE
CERTIFICATE OF CORRECTION

PATENT NO. : 4,203,891
DATED : May 20, 1980
INVENTOR(S) : Gail A. Rock

It is certified that error appears in the above–identified patent and that said Letters Patent are hereby corrected as shown below:

Column 1, line 63, change "Th" to --The--.

Column 2, line 58, change "oxylates" to --oxalates--.

Column 3, line 26, change "anticaogulant" to --anticoagulant--; and line 67, delete the word "of".

Column 4, Table 2, line 2 thereof, insert the word --heparin-- before "at time of donation".

Column 5, line 23, change "Th" to --The--.

Column 6, Table 6, line 3 under the column "CPD + Heparin", the "% Recovery" should be changed from "74.1" to --73--.

Claim 1, line 9, change "flood" to --blood--.

Signed and Sealed this

Sixth Day of January 1981

[SEAL]

Attest:

SIDNEY A. DIAMOND

Attesting Officer       Commissioner of Patents and Trademarks